United States Patent [19]

Baer et al.

[11] 4,287,099

[45] Sep. 1, 1981

[54] PREPARATION OF CATALYSTS FOR THE HYDROGENATION OF ACETYLENE-ALCOHOLS

[75] Inventors: Karl Baer, Weinheim; Wolfgang Reiss, Ludwigshafen; Wolfgang Schroeder, Bad Durkheim; Dieter Voges, Mannheim, all of Fed. Rep. of Germany

[73] Assignee: BASF Aktiengesellschaft, Fed. Rep. of Germany

[21] Appl. No.: 143,486

[22] Filed: Apr. 24, 1980

[30] Foreign Application Priority Data

Apr. 27, 1979 [DE] Fed. Rep. of Germany ....... 2917018

[51] Int. Cl.$^3$ .................. B01J 21/04; B01J 23/72; B01J 23/84; B01J 23/88
[52] U.S. Cl. .................................. 252/465; 252/470; 568/861
[58] Field of Search ................. 252/465, 470; 568/861

[56] References Cited

U.S. PATENT DOCUMENTS

| | | | |
|---|---|---|---|
| 3,444,099 | 5/1969 | Taylor et al. | 252/465 |
| 3,449,445 | 6/1969 | Wetherill | 568/861 |
| 4,048,116 | 9/1977 | Voges et al. | 252/470 |

*Primary Examiner*—W. J. Shine
*Attorney, Agent, or Firm*—Keil & Witherspoon

[57] ABSTRACT

A process for the preparation of a hydrogenation catalyst which contains the oxides of the metals nickel, copper, molybdenum and aluminum and/or iron, and may or may not contain manganese oxide, by precipitating a solution of salts of the metals with an alkali metal carbonate at from 35° to 95° C. and a pH of from 5 to 9 and heating the precipitate at from 350° to 700° C., the amount of the metal salts being selected so that the catalyst contains from 5 to 70 percent by weight of aluminum oxide and/or iron oxide, the remainder being principally nickel oxide and, based on nickel oxide, from 20 to 40 percent by weight of copper oxide, from 0.5 to 6 percent by weight of molybdenum oxide and from 0 to 10 percent by weight of manganese oxide.

3 Claims, No Drawings

PREPARATION OF CATALYSTS FOR THE HYDROGENATION OF ACETYLENE-ALCOHOLS

The present invention relates to a process for the preparation of hydrogenation catalysts and to the use of these catalysts for the hydrogenation of acetylene-alcohols.

U.S. Pat. No. 3,449,445 discloses that butyne-1,4-diol can be hydrogenated, with good yields, to butane-1,4-diol, by using a supported catalyst which contains the metals nickel, copper and manganese on silica gel. Hydrogenation catalysts of this type have only a limited life, since the silica gradually dissolves. This in turn has the adverse effect that in sustained operation silicon dioxide deposits in vaporizers and pipelines and can only be removed from these by expensive mechanical methods.

Better results are obtained with the unsupported catalysts which are described in German Laid-Open Application DOS No. 2,536,273 and which contain the oxides of the metals nickel, copper, molybdenum and manganese. These catalysts are prepared by precipitating a solution of the metal salts with sodium carbonate, filtering the carbonate suspension, and washing, drying and heating the filter residue. After having been molded, and subjected to a reductive pretreatment, they exhibit a high activity and high selectivity when used in industrial operation, but their life is again not satisfactory. Thus, in sustained industrial operation it has been found that these oxide mixtures, employed as extrudates or tablets, do not retain their shape and instead disintegrate prematurely. This disadvantage cannot be avoided by changing the conditions of preparation of the catalyst.

It is an object of the present invention to provide catalysts which are suitable for the hydrogenation of acetylene-alcohols and which, in addition to having a high activity and high selectivity, have the industrially important advantage of a long life.

We have found that this object is achieved and that, in preparing a hydrogenation catalyst, containing the oxides of the metals nickel, copper and molybdenum, with or without manganese, by precipitating a solution of salts of the metals with an alkali metal carbonate, filtering the resulting suspension and washing, drying and heating the filter residue, the molybdenum being preferably added as ammonium molybdate prior to drying, particularly advantageous results in respect of the desired properties of the catalyst are obtained if an aluminum salt and/or iron salt is added to the metal salt solution, the precipitation is carried out at from 35° to 95° C. and a pH of from 5 to 9 and the heating is carried out at from 350° to 700° C., and the amount of metal salts is so chosen that, after heating, the catalyst consists of from 5 to 70 percent by weight of aluminum oxide and/or iron oxide, the remainder being principally nickle oxide and, based on nickel oxide, from 20 to 40 percent by weight of copper oxide, from 0.5 to 6 percent by weight of molybdenum oxide and from 0 to 10 percent by weight of manganese oxide.

The process for the preparation of the novel advantageous hydrogenation catalysts may be carried out, for example, by mixing an aqueous solution containing all the metal salts simultaneously with an aqueous alkali metal carbonate solution, whilst stirring, whereupon the metals precipitate in the form of a carbonate/hydroxide mixture. Examples of metal salts used are the nitrates, sulfates and acetates of the metals mentioned, whilst the preferred alkali metal carbonate is sodium carbonate.

The aqueous metal salt solution contains, for example, from 30 to 40, preferably from 34 to 38, percent by weight of metal salt. The strength of the alkali metal carbonate solution is, for example, from 10 to 20 percent by weight, preferably from 15 to 20 percent by weight. The precipitation is carried out at from 35° to 95° C., preferably from 50° to 90° C., at a pH of from 5 to 9, preferably of around 7. After thorough mixing, the carbonate suspension is filtered and the filter residue is washed with water until free from anions and is dried at up to 120° C., for example in a drying oven or a spray dryer. Preferably, the molybdenum is added, as ammonium molybdate, to the moist filter cake.

The dry carbonate mass obtained is heated at from 350° to 700° C., preferably from 400° to 600° C. Heating is terminated when no further significant loss in weight occurs at the temperature employed. This gives a catalyst material which on heating to 900° C. loses from 2 to 10% in weight, and which contains from 5 to 70, preferably from 20 to 60, percent by weight of aluminum oxide and/or iron oxide, the remainder being principally nickel oxide, and, based on nickel oxide, from 20 to 40, preferably from 28 to 37, percent by weight of copper oxide, from 0.5 to 6, preferably from 1 to 5, percent by weight of molybdenum oxide and from 0 to 10, preferably from 0 to 8.5, percent by weight of manganese oxide. In addition to these constituents, the catalysts may also contain small amounts, for example from 0.05 to 1.5 percent by weight, of other metal salts, eg. sodium oxide.

It is advantageous to mold the catalyst before use, ie. to tablet or extrude it by a conventional method. For example, the catalyst is tableted by mixing it with a tableting assistant, eg, graphite, and then producing the tablets on a tableting press. The tablets, of size 4.75×4.75 mm, have a tap density of from 900 to 1,200 g/l, a porosity (determined by water absorption) of from 0.30 to 0.56 cm$^3$/g and a hardness of from 4,000 to 5,000 kg/cm$^2$.

It is also possible to produce extrudates from the catalyst by kneading it with water, extruding the mixture, drying it and heating it at 500° C. In general, this gives catalysts of lower density, for example of 760 g/l, the porosity being 0.6 cm$^3$/g and the cutting hardness 25 N.

The catalysts obtainable by the novel process are advantageously subjected to a conventional reductive pretreatment before being employed as hydrogenation catalysts. For example, the catalyst is treated, for this purpose, for from about 20 to 40 hours at from 230° to 280° C. with hydrogen.

The novel catalysts are valuable hydrogenation catalysts, which are especially suitable for the hydrogenation of acetylene-alcohols, eg. butyne-1,4-diol, hexyne-2,5-diol, 5-dialkylaminopent-3-yn-2-ols and propargyl alcohol. The acetylene-alcohols are reduced in a conventional manner over the catalyst (which has been pretreated with hydrogen), at from about 40° to 180° C. under a hydrogen pressure of from about 30 to 320 bar. Compared with the results previously obtained in the hydrogenation of acetylene-alcohols, the use of the catalysts according to the invention gives higher throughputs with similar yield and longer catalyst life. Furthermore, the reduction can be carried out at relatively low temperatures. The novel catalysts also exhibit improved selectivity.

EXAMPLE (a) Preparation of the catalyst:

A 20 percent strength aqueous sodium carbonate solution and an aqueous metal nitrate solution, in which the metal nitrate contents correspond to 4.7% of NiO, 1.57% of CuO, 0.47% of $Mn_3O_4$ and 4.5% of $Al_2O_3$, and which has a density of 1.4 g/cm³, are passed simultaneously into a stirred vessel, in the vicinity of a stirrer. The stirred vessel is equipped with an overflow and has a capacity of 20 liters. The metal salt solution is introduced as a constant stream, at a rate of 20 l/h. The temperature in the precipitation vessel is kept at from 50° to 95° C., preferably at 50° C., and the sodium carbonate solution is introduced at a rate such that the pH, measured by means of a glass electrode, is kept at 7.0

The carbonate suspension which overflows is collected and stored at 50° C. Before being filtered, the suspension is stirred for at least half an hour in the collecting vessel, in order to achieve homogeneous dispersion. In the course thereof, the pH rises to 7.2–7.5. The precipitate is filtered off and washed with fully deionized water. Ammonium molybdate is now worked into the moist filter cake, in an amount equivalent to 2 percent by weight of $MoO_3$, based on the residue after ignition. The filter cake is then dried at 120° C. in a drying oven or in a conventional spray dryer. The dry material obtained contains the above metals as a hydroxide/carbonate mixture and in addition contains only about 0.84% of $Na_2O$ and 0.04% of $NO_3$. The hydroxide/carbonate mixture is then heated for 1.5 hours at 500° C., resulting in a weight loss of 29%. The catalyst thus obtained contains 38.6 percent by weight of NiO, 12.9 percent by weight of CuO, 36.9 percent by weight of $Al_2O_3$, 3.91 percent by weight of $Mn_3O_4$, 1.9 percent by weight of $MoO_3$ and 0.8 percent by weight of $Na_2O$. A sample of the catalyst, when heated at 900° C., loses 5 percent in weight.

(b) Use of the catalyst for the hydrogenation of butyne-1,4-diol

The catalyst powder, obtained as described in section (a), is mixed with 3% of graphite powder in a mixing vessel, and the mixture is tableted in a press. The degree of filling of the press cavities, and the pressure employed, are selected so that the finished tablets weigh 1,030 grams per liter. The tablets have a porosity of 0.39 cm³/g and a bursting pressure of 400 N/cm².

0.5 liter of the catalyst tablets are introduced into a pressure-resistant reaction tube and are treated at 260° C., under atmospheric pressure, with hydrogen in a stream of nitrogen, at a rate which keeps the temperature below 270° C. Finally, a stream of hydrogen is passed over the catalyst for 12 hours at 270° C. The catalyst is then cooled to 30° C. and wetted with water. An 8.2 percent strength aqueous solution of butyne-1,4-diol, which additionally contains 38.8% of butanediol, 0.2% of formaldehyde and 0.3% of butanol, is then passed over the catalyst at a rate of 0.46 kg of butynediol/liter of catalyst/h, the flow rate of liquid being 40 m³/m²/h and that of the gas 30 m³/m²/h. The reaction temperature is 140° C. and the pressure 260 bar. Butanediol is obtained in a yield of 98.5%.

We claim:

1. A process for the preparation of a hydrogenation catalyst containing the oxides of the metals nickel, copper and molybdenum, with or without manganese, by precipitating a solution of salts of the metals with an alkali metal carbonate, filtering the resulting suspension and washing, drying and heating the filter residue, wherein an aluminum salt and/or iron salt is added to the metal salt solution, the precipitation is carried out at from 35° to 95° C. and a pH of from 5 to 9 and the heating is carried out at from 350° to 700° C., and the amount of metal salts is so chosen that, after heating, the catalyst consists of from 5 to 70 percent by weight of aluminum oxide and/or iron oxide, the remainder being principally nickel oxide and, based on nickel oxide, from 20 to 40 percent by weight of copper oxide, from 0.5 to 6 percent by weight of molybdenum oxide and from 0 to 10 percent by weight of manganese oxide.

2. The process of claim 1, wherein the catalyst, after heating, consists of from 20 to 60 percent by weight of aluminum oxide and/or iron oxide, the remainder being principally nickel oxide and, based on nickel oxide, from 28 to 37 percent by weight of copper oxide, from 1 to 5 percent by weight of molybdenum oxide and from 0 to 8.5 percent by weight of manganese oxide.

3. The process of claim 1 or 2, wherein the molybdenum is added as ammonium molybdate prior to drying the filter residue.

* * * * *